US00RE37106E

(19) United States
(12) Reissued Patent
Starzewski

(10) Patent Number: US RE37,106 E
(45) Date of Reissued Patent: Mar. 20, 2001

(54) PROCESS FOR THE PREPARATION OF STYRENE DERIVATIVES EXTENDED AT THE DOUBLE BOND BY ETHYLENE AND HAVING A DOUBLE BOND REMAINING IN THE EXTENSION CHAIN FORMED AND NEW STYRENE DERIVATIVES EXTENDED WITH ETHYLENE

(75) Inventor: Karl-Heinz Aleksander Ostoja Starzewski, Bad Vilbel (DE)

(73) Assignee: Bayer Aktiengesellschaft, Leverkusen (DE)

(21) Appl. No.: 08/394,538

(22) Filed: Feb. 22, 1995

Related U.S. Patent Documents

Reissue of:
(64) Patent No.: 5,180,872
Issued: Jan. 19, 1993
Appl. No.: 07/704,751
Filed: May 23, 1991

U.S. Applications:
(60) Continuation of application No. 08/145,377, filed on Oct. 29, 1993, now abandoned, which is a division of application No. 08/084,379, filed on Jun. 29, 1993, now Pat. No. Re. 34,706.

(30) Foreign Application Priority Data

Jun. 6, 1990 (DE) ..... 40 18 068

(51) Int. Cl.[7] ..... C10L 1/16; C07C 15/40; C07C 49/76

(52) U.S. Cl. ..... 585/11; 585/435; 568/332

(58) Field of Search ..... 585/435, 538, 585/11; 568/331, 332, 335; 570/128, 186, 189

(56) References Cited

U.S. PATENT DOCUMENTS

| | | | | |
|---|---|---|---|---|
| 4,620,021 | | 10/1986 | Starzewski | 556/19 |
| 4,642,405 | | 2/1987 | Kaufhold | 585/435 |
| 4,709,109 | | 11/1987 | Sperling et al. | 585/438 |
| 4,894,383 | | 1/1990 | Holmwood et al. | 514/383 |
| 4,956,123 | * | 9/1990 | Sanada et al. | 260/408 |
| 4,999,440 | | 3/1991 | Holmwood et al. | 549/556 |
| 5,026,675 | | 6/1991 | Braca et al. | 502/159 |

FOREIGN PATENT DOCUMENTS

| | | |
|---|---|---|
| 3228865 | 9/1984 | (DE) . |
| 0235714 | 9/1987 | (EP) . |

OTHER PUBLICATIONS

Kazi et al, The initiation of Cyclization With 4–substituted Cyclohexynyl Cations, Tetrahedron Letters, vol. 26, No 24, pp. 2921–2924, 1985.*

High Polymers, vol. 18, John Wiley & sons, 1964, p. 1 et seq, Chapter 1, Theory of copolymerization, pp. 5–7 & 27 et seq.

Journal of the American Chemical Society, vol. 100, No. 7, Mar. 29, 1978, pp. 2181–2190.

* cited by examiner

*Primary Examiner*—Ponnathapura Achutamurthy
(74) *Attorney, Agent, or Firm*—Norris, McLaughlin & Marcus P.A.

(57) ABSTRACT

The title compounds can be prepared by reaction of a styrene derivative with ethylene in the presence of a nickel catalyst which carries a phosphorus-oxygen chelate ligand, at a temperature of 20° to 160° C. and an ethylene pressure of 1 to 200 bar. Styrene derivatives extended with ethylene, of the formula

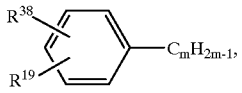

in which $R^{19}$ denotes hydrogen, $C_1$–$C_4$-alkyl, vinyl or chlorine and $R^{38}$ denotes $C_1$–$C_4$-alkyl, $C_2$–$C_4$-alkenyl, $C_2$–$C_7$-acyl, flourine, chlorine or bromine and m assumes values of 4–104, with the exception of compounds wherein $R^{19}$ denotes hydrogen and $R^{38}$ denotes i-butyl or benzoyl, and m assumes the value 4, are new.

3 Claims, No Drawings

PROCESS FOR THE PREPARATION OF STYRENE DERIVATIVES EXTENDED AT THE DOUBLE BOND BY ETHYLENE AND HAVING A DOUBLE BOND REMAINING IN THE EXTENSION CHAIN FORMED AND NEW STYRENE DERIVATIVES EXTENDED WITH ETHYLENE

Matter enclosed in heavy brackets [ ] appears in the original patent but forms no part of this reissue specification; matter printed in italics indicates the additions made by reissue.

*This application is a continuation of application Ser. No. 08/145,377, filed Oct. 29, 1993, now abandoned, which is a division of Ser. No. 08/084,379, filed Jun. 29, 1993, which is an allowed reissue 34,706 of Ser. No. 07/704,751, filed May 23, 1991, now U.S. Pat. No. 5,180,872.*

BACKGROUND OF THE INVENTION

The invention relates to a process for the reaction of styrene derivatives with ethylene in the presence of a nickel catalyst which carries a phosphorus-oxygen chelate ligand, styrene derivatives being obtained which are extended with ethylene at the olefinic double bond and in which a double bond remains in the extension chain formed.

Such styrene derivatives extended with ethylene are interesting intermediates which, owing to the double bond remaining in the extension chain, are suitable as precursors for graft polymers, for example with methyl methacrylate or maleic anhydride, or polymer-analogous reactions can be carried out using them. The styrene derivative employed according to the invention can moreover carry the substituents mentioned further below, which make possible other reactions or introduce other properties into a polymer. Of particular interest are products obtainable according to the invention in which the styrene derivative carries a further vinyl group, i.e. is, for example, divinylbenzene. In this case, mainly only one vinyl group is extended. The extended styrene derivatives formed in the course of this are bifunctional; they carry two olefinic double bonds of different reactivity. The unextended vinyl group can then be utilised in a manner known per se for styrene-analogous homo- or copolymerisations. The polymers produced therefrom furthermore carry their poly(oligo)ethylene side chains from the extension according to the invention bonded via the aromatic compounds and are thus poly(oligo)ethylene-modified. Graft reactions, derivatisations, cross-linkings and other reactions can then be carried out on the double bonds of these side chains.

SUMMARY OF THE INVENTION

A process for the preparation of styrene derivatives extended at the double bond with ethylene and having a double bond remaining in the extension chain formed has been found, which is characterised in that a styrene derivative is reacted with ethylene in the presence of a nickel catalyst which carries a phosphorus-oxygen chelate ligand, at a temperature of 20° to 160° C. and an ethylene pressure of 1 to 200 bar.

DETAILED DESCRIPTION OF THE INVENTION

A relatively large number of nickel catalysts which carry a phosphorus-oxygen chelate ligand and which can be employed according to the invention are known to the person skilled in the art.

Preferentially, the reaction is carried out in the presence of a nickel catalyst which can be prepared by reaction of a nickel(O) compound, or a compound which can be converted in situ to a nickel(O) compound, with a phosphorus compound of the formula (I)

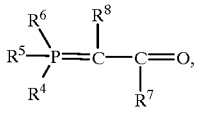

in which $R^4$, $R^5$, $R^6$, $R^7$ and $R^8$ independently of one another denote straight-chain or branched $C_1$–$C_{20}$-alkyl, $C_2$–$C_{20}$-alkenyl, $C_1$–$C_{20}$-alkoxy, $C_3$–$C_8$-cycloalkyl, $C_6$–$C_{12}$-aryl, $C_6$–$C_{12}$-aryloxy, $C_7$–$C_{15}$-aralkyl or $C_7$–$C_{15}$-aralkoxy, where $R^7$ can additionally denote hydrogen and $R^8$ can additionally denote hydrogen, acyl or sulphonate or nickel catalysts which can be prepared by reaction of a nickel(O) compound, or a compound which can be converted in situ to a nickel(O) compound, with an adduct of a quinoid compound or maleic anhydride and a phosphine of the formula (II)

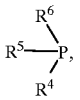

in which $R^4$, $R^5$ and $R^6$ have the meaning mentioned.

Such phosphorus ylide-nickel compounds can be employed both individually and as a mixture of several of them.

Preferentially, $R^4$ has the meaning of optionally substituted $C_6$–$C_{12}$-aryl. Additionally preferentially, in the preparation of the above catalysts from a nickel(O) compound or a compound which can be converted in situ to a nickel(O) compound, a compound of the formula (I) and additionally a compound of the formula (III)

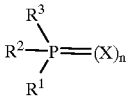

are used as starting compounds, in which $R^1$, $R^2$ and $R^3$ independently of one another denote straight-chain or branched $C_1$–$C_{20}$-alkyl, $C_1$–$C_{20}$-alkoxy, $C_3$–$C_8$-cycloalkyl, $C_2$–$C_{20}$-alkenyl, di-($C_1$–$C_4$-alkyl)amino, $C_6$–$C_{12}$-aryl, $C_6$–$C_{12}$-aryloxy, $C_7$–$C_{15}$-aralkyl or $C_7$–$C_{15}$-aralkoxy, X denotes doubly bonded oxygen, the doubly bonded group $NR^9$ or the doubly bonded group

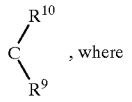

, where $R^9$ and $R^{10}$ independently of one another denote hydrogen, silyl, acyl, chlorophenyl, nitrophenyl, $C_1$–$C_6$-alkylphenyl, cyano, phenyl-$C_2$–$C_6$-alkenyl or $R^1$, and n assumes the value zero or one.

In the preparation of the above catalysts, starting from a nickel(O) compound, or a compound which can be converted in situ to a nickel(O) compound, and an adduct of a quinoid compound or maleic anhydride and a compound of the formula (II), it is additionally still preferred to start from a compound of the formula (III).

Particularly preferentially, the reaction is carried out in the presence of a nickel catalyst which is obtained by reaction of a nickel(O) compound with phosphorus compounds of the formulae (IV)

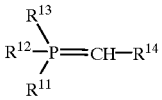

and (V)

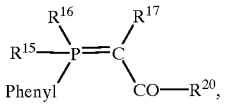

in which $R^{11}$, $R^{12}$ and $R^{13}$ independently of one another denote $C_1$–$C_8$-alkyl, phenyl or benzyl, $R^{14}$ represents hydrogen, $C_1$–$C_8$-alkyl or phenyl, $R^{15}$, $R^{16}$ and $R^{17}$ independently of one another denote $C_1$–$C_8$-alkyl or phenyl, where $R^{17}$ can additionally denote hydrogen or acyl, and $R^{20}$ denotes phenyl or $C_1$–$C_4$-alkyl, or a nickel catalyst which can be prepared by reaction of a nickel(O) compound, or a compound which can be converted in situ into a nickel(O) compound, with an adduct of benzoquinone or maleic anhydride and a phosphine of the formula (VI)

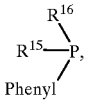

in which $R^{15}$ and $R^{16}$ have the meaning mentioned, and a compound of the formula (IV).

$R^{20}$ is preferentially phenyl.

0 to 4 mol of the compound of the formula (III) and 1 to 4 mol of the compound of the formula (I) are employed per mole of nickel(O) compound to prepare the catalyst, preferably about 1 mol of the compound of the formula (III) or (IV) and about 1 mol of the compound of the formula (I) or (V) per mol of the nickel(O) compound. Identical molar ratios apply if a compound of the formula (I) or (V) is replaced by a quinone/phosphine adduct or a maleic anhydride/phosphine adduct of the type described.

The temperature for the preparation of the catalyst is 0° to 100° C., preferably 20° to 70° C. The preparation is carried out with the exclusion of oxygen, preferably in a solvent, which must be inert to the reactants, such as benzene, toluene, cyclohexane or n-hexane. After its preparation, the catalyst is usually isolated as a solid by filtering, the solution being concentrated and/or cooled beforehand as required. However, the catalyst can also be employed directly without isolation, i.e. as a solution or suspension, for the reaction according to the invention.

Nickel(O) compounds which may be mentioned by way of example are Ni(cyclooctadiene)$_2$ and Ni(allyl)$_2$. Examples of nickel compounds which can be converted in situ to nickel(O) compounds are: Ni acetylacetonate, Ni octanoate and Ni stearate, which can be reduced with the aid of customary reducing agents, such as borohydride, alumino-hydride, aluminium alkyl or organolithium compounds.

Examples of alkyl, preferably $C_1$–$C_8$-alkyl, which can be straight-chain or branched are: methyl, ethyl, propyl, isopropyl, butyl, isobutyl, tert-butyl, the isomeric pentyls, hexyls, octyls, decyls, dodecyls, hexadecyls and eicosyls. Particularly preferred alkyl has 1 to 4C atoms.

Examples of $C_1$–$C_{20}$-alkoxy which can be straight-chain or branched are: methoxy, ethoxy, propoxy, isopropoxy, butoxy, isobutoxy, tert.-butoxy, the isomeric pentyloxys, hexyloxys, octyloxys, decyloxys, dodecyloxys and eicosyloxys. Preferred alkoxy has 1 to 8C atoms, particularly preferred alkoxy 1 to 4C atoms.

Examples of $C_3$–$C_8$-cycloalkyl are: cyclopropyl, cyclobutyl, cyclopentyl, cyclohexyl, methyl cyclopentyl, methyl cyclohexyl, cycloheptyl, cyclooctyl.

Examples of $C_6$–$C_{12}$-aryl are: phenyl, naphthyl, biphenyl. Preferred aryl is phenyl.

Examples of $C_2$–$C_{20}$ alkenyl are: vinyl, propenyl, allyl, butenyl, pentenyl, hexenyl, octenyl, decenyl or eicosenyl and their branched isomers.

Examples of $C_6$–$C_{12}$-aryloxy are: phenoxy, naphthyloxy, biphenyloxy. Phenoxy is preferred.

Examples of $C_7$–$C_{15}$-aralkyl are: benzyl, phenylethyl, phenylpropyl, naphthyl-methyl, preferably benzyl.

Examples of $C_7$–$C_{15}$-aralkoxy are: benzyloxy, phenylethyloxy, phenyl-propyloxy, naphthyl-methyloxy, preferably benzyloxy.

Examples of di-($C_1$–$C_4$-alkyl)-amino are: dimethylamino, diethylamino, dipropylamino, methylbutylamino, ethylbutylamino etc.

Examples of silyl are tri-$C_1$–$C_4$-alkylsilyl, triphenylsilyl or mixed trisubstituted alkylphenyl-silyls, preferably tri-$C_1$–$C_4$-alkyl-silyls, such as trimethylsilyl, triethylsilyl etc.

Acyl is $C_1$–$C_8$-alkylcarbonyl or $C_6$–$C_{12}$-arylcarbonyl which can be substituted in the manner mentioned below, such as acetyl, propionyl, butyryl, $C_5$-alkyl-carbonyl, $C_8$-alkylcarbonyl, benzoyl, substituted benzoyl or naphthylcarbonyl. Preferred acyl is substituted or unsubstituted $C_1$–$C_4$-alkyl-carbonyl or benzoyl. Acetyl or benzoyl are particularly preferred.

The said substituents can be monosubstituted to trisubstituted, preferably monosubstituted or disubstituted, particularly preferably monosubstituted, by $C_1$–$C_4$-alkyl, by $C_1$–$C_4$-alkoxy, by $C_6$–$C_{12}$-aryl, or by $C_6$–$C_{12}$-aryloxy or nitro, preferably by $C_1$–$C_4$-alkyl, by $C_1$–$C_4$-alkoxy, or by phenyl or phenoxy, it being possible in the case of multiple substitution for the substituents to be different from the said enumeration. In this sense, tolyl, for example, is additionally understood as aryl.

Suitable quinoid compounds are o- or p-quinoid compounds of the benzene and naphthalene series and also anthraquinones, which can additionally be substituted in the manner described above. p-Benzoquinone, 1,4-naphthoquinone and 9,10-anthraquinone may be mentioned by way of example.

The preferred nickel compounds containing phosphorus-oxygen chelate ligands are, according to present knowledge, in agreement with the formula (VII)

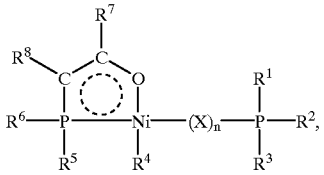

in which

X, n and $R^1$ to $R^8$ have the meanings mentioned above.

In the case in which a compound of the formula (I) is replaced, for example, by a maleic anhydride/phosphine adduct of the type described, the formula (VII) becomes the formula below (VIII)

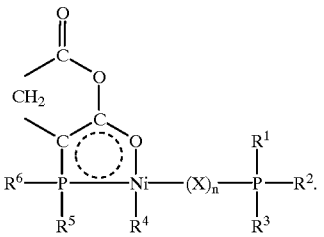

A general structural feature of the nickel catalysts which can be employed according to the invention and which carry a phosphorus-oxygen chelate ligand is the following configuration

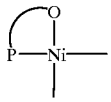

Preferred radicals $R^1$, $R^2$ and $R^3$ are $C_1$–$C_8$-alkyl, cyclohexyl, phenyl, tolyl, benzyl, di-($C_1$–$C_4$-alkyl)-amino, phenoxy and $C_1$–$C_4$-alkoxy.

$R^4$ is preferably $C_6$–$C_{12}$-aryl, particularly preferably phenyl.

$R^5$, $R^6$, $R^7$ and $R^8$ are independently of one another preferably cyclohexyl, phenyl, tolyl, benzyl, vinyl and $C_1$–$C_4$-alkyl.

$R^7$ is moreover preferably hydrogen or $C_1$–$C_4$-alkoxy, $R^8$ is moreover preferably hydrogen, acetyl, benzoyl or the sulphonate group.

$R^9$ and $R^{10}$ are preferably hydrogen, $C_1$–$C_8$-alkyl, phenyl, chlorophenyl, nitrophenyl, $C_1$–$C_6$-alkylphenyl, trimethylsilyl, cyano, $C_2$–$C_6$-alkenyl and phenyl-$C_2$–$C_6$-alkenyl.

0.01 to 100 mmol of nickel catalyst per mol of styrene derivative, preferably 0.1 to 10 mmol of nickel catalyst, particularly preferably 0.2 to 5 mmol of nickel catalyst, are employed for the reaction according to the invention. It is furthermore possible to activate these nickel catalysts by organoaluminium compounds, preferably alkyl- or alkoxy-aluminiu compounds.

The process according to the invention is carried out at a temperature of 20° to 160° C., preferably at 30° to 140° C., particularly preferably at 40° to 120° C., very particularly preferably at 50° to 100° C.

It is carried out at an ethylene pressure of 1 to 200 bar, preferably 2 to 50 bar, particularly preferably 3 to 25 bar.

According to the invention, a styrene derivative of the formula (IX)

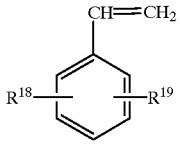

is employed in which $R^{18}$ is hydrogen, $C_1$–$C_4$-alkyl, $C_2$–$C_4$-alkenyl, $C_2$–$C_7$-acyl, fluorine, chlorine or bromine and $R^{19}$ is hydrogen, $C_1$–$C_4$-alkyl, vinyl or chlorine.

Examples of $C_2$–$C_7$-acyl are; acetyl, propionyl, butyryl, benzoyl, preferably benzoyl.

Preferentially, styrene derivatives of the formula (X)

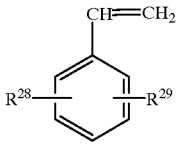

are employed in which $R^{28}$ is hydrogen, methyl, ethyl, i-butyl, $C_2$–$C_7$-acyl, vinyl or chlorine and $R^{29}$ is hydrogen, vinyl, methyl or chlorine.

Particularly preferentially, styrene or divinylbenzene are employed.

The styrene derivatives to be employed according to the invention can be employed both in pure form and as a technical mixture. An important example of this latter case is technical divinylbenzene, which additionally contains ethyl-styrene and; or diethyl-benzene. Further benzoyl styrenes, e.g. 3-benzoyl styrene, can be mentioned.

The process according to the invention is Carried out in the liquid phase. In this case, the reaction can basically be carried out without co-use of an inert solvent if the styrene derivative is liquid.

In many cases, the process according to the invention is carried out in the presence of an inert solvent. Suitable examples of such inert solvents are: n-hexane, cyclohexane, petroleum ether, ligroin, benzene, toluene, chlorobenzene, acetone, dimethylformamide and other solvents which are not attacked under the reaction conditions, preferably cyclohexane or toluene.

The inert solvent is employed in an amount by weight which is 0.1 to 100 times, preferably 0.5 to 20 times, relative to the styrene derivative.

The reaction product of the process according to the invention is in general initially a homologous series of extended styrene derivatives in which the extension comprises one molecule of ethylene per molecule of the basic styrene derivative or two or more molecules of ethylene per mol of the basic styrene derivative and in which a double bond remains in the extension chain. The individual components of the styrene-ethylene reaction can be represented by the following formulae:

(XIa)

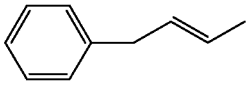

(XIb)

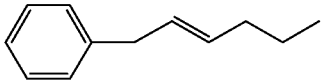

(XIc)

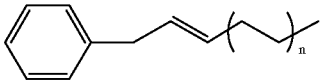

Formula (XIa) in this connection represents the case styrene/ethylene =1:1, formula (XIb) represents the case styrene/ethylene =1:2, and formula (XIc) represents the general case styrene/ethylene =1:1 +n, where n principally assumes values from 0 (zero) to 100, in particular 0 to 30, very particularly 0–10.

As a result of isomerisation reactions, homologous series of isomeric products are also formed in the process according to the invention, which appear to be in agreement with the following formulae:

(XIIa)

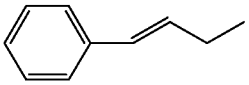

or (XIIb)

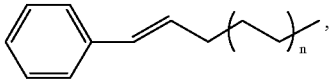

(XIII)

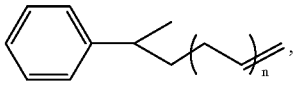

(XIV)

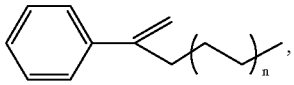

(XV)

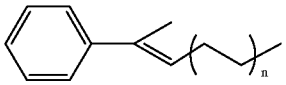

and (XVI)

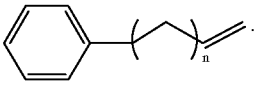

(XV)

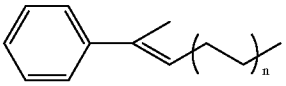

and

-continued (XVI)

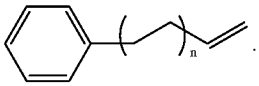

With olefinically unsaturated compounds, owing to the cis-trans isomerism known to the person skilled in the art, the corresponding cis isomers always also occur in addition to the above compounds of the formulae (XI) to [(XVII)] (*XVI*) represented as trans isomers.

In the formulae (XI a-c), (XII a and b) and (XIII) to (XVII), the bending points and end points of the bent line (=extension chain) denote, in a manner familiar to the person skilled in the art, C atoms which have the necessary number of H atoms. As a result, for example, the following detailed notation results for the formulae (XIa) and (XIII)

(XIa)

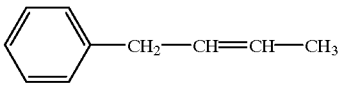

or (XIII)

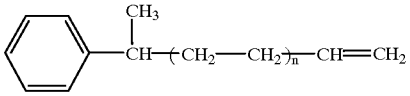

In the formulae (XI) to (XVII), the ring substitution as in formula (IX) or (X) has been left out for the sake of clarity.

The whole of the process product of the process according to the invention having a double bond remaining in the branched or unbranched extension chain can thus be represented by the formula (XVII)

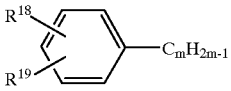

in which the index m assumes the value of the above index [n+4] *2n+4* and $R^{18}$ and $R^{19}$ have the above scope of meaning.

In the manner shown above, this is in general the mixture of the homologues coming under the formula (XVII).

Polyolefins occur as by-products.

Such a product mixture can be separated into individual components or into fractions in a manner known to the person skilled in the art, for example by chromatographic separation, fractional distillation or precipitation.

The process according to the invention is surprising insofar as using the nickel catalyst to be employed, with which, as is known, ethylene can be polymerised, polyethylene formation in this case now becomes the side reaction. Polystyrene formation is also almost completely suppressed. The homologous series of styrene/ethylene coupling products becomes the principal reaction product, a shift to higher or lower molecular weights taking place according to the methods known for polyethylene molecular weight control. Molecular weights below 10,000 g/mol are preferred, particularly preferably below 1,000 g/mol.

The following procedures, for example, are suitable for the process according to the invention:

a) initial introduction of the solid, suspended or dissolved catalyst (or its components) and addition of the monomers simultaneously or successively at the desired temperature;

b) initial introduction of the monomers and injection of the catalyst solution or suspension (or its components) at the desired temperature, if appropriate with subsequent heating;

c) continuous metering of the catalyst solution (or its components) and the monomers under prestated desired polymerisation conditions (pressure, temperature).

The process according to the invention can be carried out, for example, as follows: the solvent is initially introduced into an autoclave. The intended amount of styrene derivative is then added. Ethylene, on its own or mixed with an inert gas, is then pumped into the closed autoclave to the desired reaction pressure, if appropriate taking into account the pressure increase at reaction temperature. The autoclave is then heated to the desired reaction temperature and the nickel catalyst is added as a solid, as a suspension or as a solution. Preferably, a catalyst solution is pumped in simultaneously to the use of ethylene (multi-pulse process). The carrying-out of the polymerising coupling of the styrene is assisted by shaking of the autoclave or by a suitable lifting or stirring device. The ethylene can be replenished at the rate of its consumption during the reaction. After completion of the reaction, the autoclave is cooled, depressurised and opened. The reaction mixture is worked up, for example, by distillation. In this case, the optionally co-used inert solvent and the unreacted styrene derivative are separated off first, for example by distillation. The remaining reaction mixture containing the extended styrene derivatives prepared according to the invention can then be separated into individual components or into suitable fractions by fine distillation, by crystallisation or precipitation or by other separating operations. All distillations are advantageously carried out in the presence of customary stabilisers in order to suppress thermal polymerisation.

A number of styrene derivatives extended with ethylene, which can be prepared according to the invention and which have a remaining double bond in the extension chain formed, are new.

The invention therefore furthermore relates to styrene derivatives extended with ethylene, of the formula (XVIII)

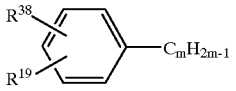

in which $R^{38}$ represents $C_1$–$C_4$-alkyl, $C_2$–$C_4$-alkenyl, $C_2$–$C_7$-acyl, fluorine, chlorine or bromine, $R^{19}$ has the above scope of meaning and m assumes values of 4 to [104] *204*, preferably [4 to 34] *6 to 64*, particularly preferably [4 to 14] *6 to 24*, preferably those of the formula (XIX)

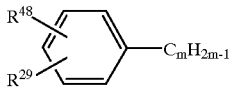

in which $R^{48}$ denotes vinyl, i-butyl or benzoyl and $R^{29}$ and m have the above scope of meaning, *particularly preferably those of the formula*

(XX)

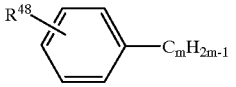

in which $R^{48}$ and m have the above scope of meaning, whereby compounds are excepted wherein $R^{19}$ and $R^{29}$, respectively, denote hydrogen, $R^{38}$ and $R^{48}$, respectively, denote i-butyl or benzoyl, and m assumes the value 4.

This means in the case of formula (XX) that m assumes values of 6 to [104] *204*, preferably 6 to [34] *64*, particularly [preferable 6 to 14] *preferably 6 to 24*, taking into account that the difference in the lower limit of m (6 instead of 4) makes just one ethylene ($C_2$) unit.

Of course, the new styrene derivatives extended with ethylene, of the formulae (XVIII), (XIX), and (XX) also include the mixture of the homologous series formed from them.

The new substances mentioned likewise also include the mixture with the technical impurities of the basic styrenes and/or with the homologous reaction products extended with ethylene in the case in which styrene derivatives present in technical purity have been used as starting materials; this case has been illustrated further above for technical divinylbenzene.

EXAMPLE 1

Catalyst preparation [NiPh($Ph_2$PCHCMeO)($Pr^i{}_3$PCHPh)]

40 mmol of bis-cyclooctadiene-nickel(O) in 250 ml of dry argon-saturated toluene were mixed under argon with 40 mmol of acetylmethylene-triphenylphosphorane and 40 mmol of triisopropyl-phosphinebenzylidene. The mixture was heated to 60° C. for about 3 hours with intensive stirring. The dark brown reaction mixture was filtered under argon and the filtrate was concentrated to dryness in vacuo. The crude catalyst thus obtained was dissolved in toluene at 60° C., hexane was added until turbidity persisted and the solution was crystallised in the cold, the crystals were isolated by Schlenk filtration, washed with hexane and dried in vacuo.

EXAMPLES 2–10

General experimental procedure

The amount of toluene mentioned in the following tables, the amount of catalyst mentioned and the amount of styrene derivative mentioned were initially introduced into an autoclave of suitable size. An amount of ethylene was then added under pressure such that the ethylene pressure indicated in the tables was attained at the reaction temperature indicated. During the reaction period indicated in the tables, ethylene was additionally added to maintain the pressure indicated. The yield was determined by weighing the residue after distillative separation of solvent and unreacted styrene derivative. The tables show the results obtained by gas chromatography relating to the percentage distribution of extended styrene derivatives (denoted as "product") and co-formed α-olefin (polyethylene by-product).

TABLE 1

(Examples 2 to 5)
Reaction of styrene derivatives in toluene with ethylene at a temperature of 80–90° C. in a 2-hour reaction

| | Catalyst | | Styrene | Ethylene | Toluene | Yield | Product | α-olefin |
|---|---|---|---|---|---|---|---|---|
| No. | Type | Amount | derivative | bar | ml | g | % | % |
| 2 | NiPh($Ph_2$PCHCMeO) ($Pr^i_3$PCHPh) | 1 mmol | 0.1 mol p-methyl-styrene | 10 | 80 | not deter-mined | 60 | 40 |
| 3 | NiPh($Ph_2$PCHCMeO ($Pr^i_3$PCHPh) | 1 mmol | 0.1 mol 3,4-dichloro-styrene | 10 | 80 | not deter-mined | 50 | 50 |
| 4 | $Ni(COD)_2$ $Ph_3$PCHCPhO $Ph_3$PO | 4 mmol | 1 mol o-chlorostyrene | 5 | 500 | 35 | 71 | 29 |
| 5 | $Ni(COD)_2$ $Ph_3$PCHCPhO $Ph_3$PO | 4 mmol | 3 mol styrene | 5 | 500 | 220 | 74 | 26 |

TABLE 2

(Examples 6 and 7)
Reaction of divinylbenzene (DVB, freshly distilled, 390 g in each case) in toluene (1,000 ml in each case) with ethylene in a 2-hour reaction; catalyst metering by multi-pulse

| | Catalyst | | Ethylene | Temp. | Yield | Product | α-olefin |
|---|---|---|---|---|---|---|---|
| No. | Type | Amount | bar | ° C. | g | % | % |
| 6 | $Ni(COD)_2$ $Ph_3$PCHCPhO $Ph_3$PO | 4 mmol in situ in 150 ml toluene | 2.5 | 90 | 173 | 89 | 11 |
| 7 | NiPh($Ph_2$PCHCPhO) ($Ph_3$P) | 4 mmol isolated in 150 ml toluene | 5.0 | 50 | 278 | 85 | 15 |

for the catalyst:
COD = cyclooctadiene;
Ph = phenyl;
Me = methyl
Product = Total amount of the extended styrene derivative obtained

TABLE 3

(Examples 8 to 10)
Reaction of divinylbenzene (DVB, freshly distilled, 390 g in each case) in toluene (1,000 ml in each case) with ethylene at 90° C. in a 2-hour reaction with 4 mmol of $Ni(COD)_2/Ph_3PCHCPhO/Ph_3PNSiMe_3$ as an in situ catalyst in 150 ml of toluene, catalyst metering: multi-pulse

| No. | Ethylene bar | Yield g | Product % | α-olefin % |
|---|---|---|---|---|
| 8 | 10 | 320 | 70 | 30 |
| 9 | 5 | 345 | 83 | 17 |
| 10 | 2.5 | 110 | 91 | 9 |

What is claimed is:

[1. A process for the preparation of styrene derivatives extended at the double bond with ethylene and having a double bond remaining in the extension chain formed, according to the formula

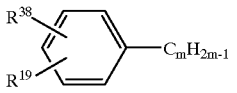

in which $R^{19}$ denotes hydrogen, $C_1$–$C_4$-alkylvinyl or chlorine, $R^{38}$ denotes $C_1$–$C_4$-alkyl, $C_2$–$C_4$-alkenyl, $C_2$–$C_7$-acyl, fluorine chlorine or bromine, and m has a value of 4 to 104, with the exception of compounds wherein $R^{19}$ is hydrogen and $R^{38}$ is isobutyl or benzyl and m has the value 4, wherein a styrene derivative is reacted with ethylene in the presence of a nickel catalyst which carries a phosphorus-oxygen chelate ligand, at a temperature of 20 to 160° C. and an ethylene pressure of 1 to 200 bar, wherein the nickel catalyst is obtained by reaction of a nickel (O) compound, or a compound which can be converted in situ to a nickel (O) compound, with a phosphorus compound of the formula (I)

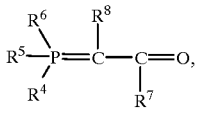

in which $R^4$, $R^5$, $R^6$, $R^7$ and $R^8$ independently of one another denote straight-chain or branched $C_1$–$C_{20}$-alkyl, $C_2$–$C_{20}$-alkenyl, $C_1$–$C_{20}$-alkoxy, $C_3$–$C_8$-cycloalkyl, $C_6$–$C_{12}$-aryl, $C_6$–$C_{12}$-aryloxy, $C_7$–$C_{15}$-aralkyl or $C_7$–$C_{15}$-aralkoxy, where $R^7$ can additionally denote hydrogen and $R^8$ can additionally denote hydrogen, acyl or sulphonate, or a nickel catalyst which can be prepared by reaction of a nickel (O) compound, or a compound which can be converted in situ to a nickel (O) compound, with an adduct of a quinoid compound or maleic anhydride and a phosphine of the formula (II)

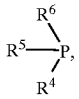

in which $R^4$, $R^5$ and $R^6$ have the meaning mentioned.]

[2. The process of claim 1, wherein for the preparation of the nickel catalyst from a nickel(O) compound or a compound which can be converted in situ into a nickel(O) compound, and from a compound of the formula (I) or from an adduct of a quinoid compound or maleic anhydride and a compound of the formula (II), a compound of the formula (III)

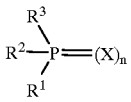

in additionally used as a starting material in which $R^1$, $R^2$ and $R^3$ independently of one another denote straight-chain or branched $C_1$–$C_{20}$-alkyl, $C_1$–$C_{20}$-alkoxy, $C_3$–$C_8$-cycloalkyl, $C_2$–$C_{20}$-alkenyl, di-($C_1$–$C_4$-alkyl)amino, $C_6$–$C_{12}$-aryl, $C_6$–$C_{12}$-aryloxy, $C_7$–$C_{15}$-aralkyl or $C_7$–$C_{15}$-aralkoxy, X denotes doubly bonded oxygen, the doubly bonded group $NR^9$ or the doubly bonded group

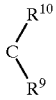

, where $R^9$ and $R^{10}$ independently of one another denote hydrogen, silyl, acyl, chlorophenyl, nitrophenyl, $C_1$–$C_6$-alkylphenyl, cyano, phenyl-$C_2$–$C_6$-alkenyl or $R^1$, and n assumes the value zero or one.]

[3. The process of claim 3, wherein the reaction is carried out in the presence of a nickel catalyst which is obtained by reaction of a nickel(O) compound, or a compound which can be converted into a nickel(O) compound in situ, with phosphorus compounds of the formulae (IV)

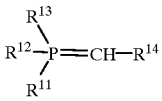

and (V)

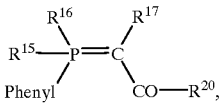

in which $R^{11}$, $R^{12}$ and $R^{13}$ independently of one another denote $C_1$–$C_8$-alkyl, phenyl or benzyl, $R^{14}$ represents hydrogen, $C_1$–$C_8$-alkyl or phenyl, $R^{15}$, $R^{16}$ and $R^{17}$ independently of one another denote $C_1$–$C_8$-alkyl or phenyl, where $R^{17}$ can additionally denote hydrogen or acyl, and $R^{20}$ denotes phenyl or $C_1$–$C_4$-alkyl, or a nickel catalyst which can be prepared by reaction of a nickel(O) compound, or a compound which can be converted in situ into a nickel(O) compound, with an adduct of benzoquinone or maleic anhydride and a phosphine of the formula (VI)

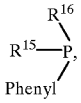

in which $R^{15}$ and $R^{16}$ have the meaning mentioned, and a compound of the formula (IV).]

[4. The process of claim 1, wherein 0.01 to 100 mmol of nickel catalyst are employed per mol of styrene derivative.]

[5. The process of claim 5, wherein 0.1 to 10 mmol of nickel catalyst are employed per mol of styrene derivative.]

[6. The process of claim 6, wherein 0.2 to 5 mmol of nickel catalyst are employed per mol of styrene derivative.]

[7. The process of claim 1, wherein a styrene derivative of the formula

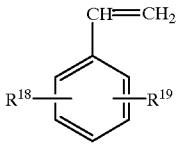

is employed in which $R^{18}$ is hydrogen, $C_1$–$C_4$-alkyl, $C_2$–$C_4$-alkenyl, $C_2$–$C_7$-acyl, fluorine, chlorine or bromine and $R^{19}$ is hydrogen, $C_1$–$C_4$-alkyl, vinyl or chlorine.]

[8. The process of claim 8, wherein a styrene derivative of the formula

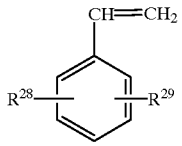

is employed in which $R^{28}$ is hydrogen, methyl, ethyl, i-butyl, $C_2$–$C_7$-acyl, vinyl or chlorine and $R^{29}$ is hydrogen, vinyl, methyl or chlorine.]

[9. The process of claim 1, which is carried out at a temperature of 30° to 160° C.]

[10. The process of claim 9, which is carried out at a temperature of 40° to 120° C.]

[11. The process of claim 10, which is carried out at a temperature of 50° to 100° C.]

*12. A styrene derivative extended with ethylene and having a double bond remaining in the extension formed, of the formula*

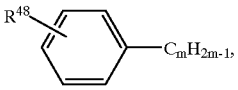

*in which*

*$R^{48}$ is i-butyl or benzoyl, and*

*m is an even number from 6 to 204.*

*13. A styrene derivative extended with ethylene and having a double bond remaining in the extension formed, of the formula*

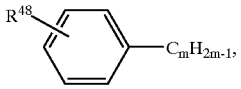

*in which*

*$R^{48}$ is vinyl, and*

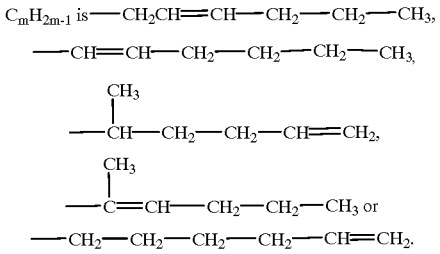

*14. A derivative according to claim 12, wherein m is up to 64.*

* * * * *